US006659970B1

United States Patent
Woodworth et al.

(10) Patent No.: US 6,659,970 B1
(45) Date of Patent: Dec. 9, 2003

(54) ADJUSTABLE DRESSING WRAP

(76) Inventors: Carol Anna Woodworth, 3828 Elmwood Ave., Louisville, KY (US) 40207; Joyce A. Bonick, 2812 Winterhaven Rd., Louisville, KY (US) 40220; Jean E. Woodworth, 101 Hillcrest Ave., Louisville, KY (US) 40206

( * ) Notice: Subject to any disclaimer, the term of this patent is extended or adjusted under 35 U.S.C. 154(b) by 150 days.

(21) Appl. No.: 09/956,384

(22) Filed: Sep. 19, 2001

Related U.S. Application Data

(60) Provisional application No. 60/233,883, filed on Sep. 20, 2000.

(51) Int. Cl.[7] ............................................. A61F 13/00
(52) U.S. Cl. ............................... 602/3; 602/42; 602/79; 128/888
(58) Field of Search ........................ 662/1, 3, 42, 60–63, 662/75–77, 79; 128/849, 855–856, 888; 604/293, 304, 308

(56) References Cited

U.S. PATENT DOCUMENTS

| | | | |
|---|---|---|---|
| 1,517,984 A | * 12/1924 | Harvey | ............................. 2/59 |
| 2,534,888 A | * 12/1950 | Vold | ................................ 2/24 |
| 2,798,489 A | * 7/1957 | Behrman | .................... 604/399 |
| 3,054,400 A | 9/1962 | Lizio | |
| 3,442,270 A | 5/1969 | Steinman | |
| 3,504,672 A | * 4/1970 | Moon | .......................... 602/75 |
| 3,752,163 A | 8/1973 | Kaplan | |
| 3,756,878 A | * 9/1973 | Willot | .......................... 156/70 |
| 3,968,803 A | 7/1976 | Hyman | |
| 4,787,381 A | 11/1988 | Hubbard et al. | |
| 4,909,243 A | 3/1990 | Frank et al. | |
| 5,010,596 A | * 4/1991 | Brown et al. | ................... 2/228 |
| 5,063,919 A | * 11/1991 | Silverberg | ..................... 602/3 |
| 5,098,331 A | 3/1992 | Corrado | |
| 5,209,801 A | * 5/1993 | Smith | ........................ 156/161 |
| 5,533,963 A | 7/1996 | Hall | |
| 5,538,502 A | 7/1996 | Johnstone | |
| 5,609,569 A | 3/1997 | Offenhartz | |
| 5,779,657 A | 7/1998 | Daneshvar | |
| 5,817,038 A | 10/1998 | Orange et al. | |
| 5,994,612 A | * 11/1999 | Watkins | ....................... 602/41 |
| 6,043,408 A | 3/2000 | Geng | |
| 6,213,968 B1 | 4/2001 | Heinz et al. | |
| 6,238,692 B1 | 5/2001 | Smith | |

FOREIGN PATENT DOCUMENTS

FR 2630908 A1 * 11/1989 ........... A61B/17/60

OTHER PUBLICATIONS

Dale Medical, Dale Abdominal Binder–Product Information www.dalemed.com, Sep. 18, 2001.
Hyperion Medical, Inc., Hyperion Tapeless Bandages—Product Information www.hyperionmedical.com, Sep. 18, 2001.
Snugs, Tape Free Wound Care—Product Information www.snugs.com, Sep. 18, 2001.
Wisdomking.com, Dermicel Montgomery Straps—Product Information www.wisdomking.com, 1999.

* cited by examiner

*Primary Examiner*—Nicholas D. Lucchesi
*Assistant Examiner*—Victor Huang
(74) *Attorney, Agent, or Firm*—Camoriano and Associates; Theresa Fritz Camoriano; Guillermo Camoriano

(57) ABSTRACT

An adjustable dressing wrap made from an elastic, porous, breathable mesh material, mounted on a framework including two substantially vertically-oriented fasteners along its left and right ends, and two substantially horizontally-extending elastic members, wherein the framework is substantially more rigid than the elastic mesh material when it is placed on the patient. The horizontally-extending elastic members may be adjusted by tightening around the body part such that the elastic mesh material may support and maintain the wound dressings in place.

9 Claims, 2 Drawing Sheets

ADJUSTABLE DRESSING WRAP

This application claims priority from Provisional Application Ser. No. 60/233,883 filed Sep. 20, 2000.

FIELD OF THE INVENTION

The present invention relates generally to medical/surgical wound care management. In particular, it relates to an improved, adjustable wrap designed to hold a primary dressing in place over a wound while minimizing stress to the adjacent skin structures.

BACKGROUND OF THE INVENTION

In current medical and surgical practice, adhesive tape is the means most commonly used to secure wound dressings, notwithstanding the fact that significant numbers of patients, particularly the elderly and diabetics, typically have sensitive skin that is damaged by the repeated application and removal of tape during the healing process. In practical terms, this undesired complication translates into a longer, more expensive recovery for these patients, since their more or less serious secondary, tape-related wounds also require treatment. Accordingly, wound care specialists advocate the use of a tapeless dressing system in the treatment of such patients.

Although the medical/surgical binders and wraps currently available to the healthcare industry unquestionably represent a significant advance in wound care management, as a group, they also exhibit a variety of shortcomings. Some may, for example, be constructed primarily of non-porous materials that trap and hold body heat and perspiration. Others may be made of relatively inelastic, more rigid materials that do not readily conform to the natural contours of the human anatomy. These products are not well-tolerated by most patients for continuous dressing support.

Some of the binders and wraps currently being marketed to the healthcare industry are said to provide individually customizable fit, but they may actually be available in one size only, or they may offer such a limited range of adjustability that exact fit is seldom possible.

When wound patients attempt physical movement, whether in bed or out, caregivers routinely report that some products fail to retain primary dressings in place as securely as needed for optimal healing to occur, thus increasing the risk of infection and prolonging the healing process and length of recovery.

Another widely noted negative concomitant of unreliable dressing support is reluctance by both acute and chronic wound patients to become fully engaged in self-care and physical therapy activities, which also retards the speed of recovery. And finally, taking into consideration the need to control spiraling healthcare costs in general, it should be noted that some wraps are constructed of materials which simply will not withstand the frequent laundering and sanitizing required for re-use. As a result, wound patients relying on these products during an extended convalescence are faced with unduly costly care.

SUMMARY OF THE INVENTION

Features of a preferred embodiment of the present invention are that it provides a greatly improved wound dressing wrap that is 1) sufficiently comfortable to permit more or less continuous use by both acute and chronic wound patients throughout recovery, however lengthy;
2) designed to permit manufacture in a range of sizes, together with the capability for independent adjustment of the circumference of the upper and lower edges as well as the vertical closing in order to provide a fully customizable fit for a wide range of patient body types;
3) easily adjusted by caregivers or the patient himself to ensure continuous security of the primary dressing materials regardless of the activity level maintained by the patient; and
4) constructed of materials that may be laundered and sanitized repeatedly without losing their original patient-friendly attributes.

The preferred embodiment of the present invention incorporates a design that is generally rectangular in shape, being substantially longer than it is wide, enabling it to encircle the traumatized anatomical part that is being treated, such as the abdomen, leg, or arm, together with the primary dressing materials. Constructed of a lightweight, stretchable material, the upper and lower edges of the wrap are casings which hold elastic members that are used to conform those edges to the dimensions of the individual patient while retaining the primary dressing materials in place over the wound site. One end of each of the two elastic members is stitched to the wrap, while the opposing end remains open, permitting each of the elastic members to be adjusted independently of the other, positioned as desired, and secured by means of hook and loop fasteners. Hook and loop fasteners are also stitched to the ends of the body of the wrap to form a secure vertical closing when pressed together. This design, incorporating three independent hook and loop closings that are each adjusted to conform to specific body dimensions, maximizes the individually customized fit of this embodiment of the present invention.

While this adjustable dressing wrap, as described here and as shown in the following drawings, was developed for use with an abdominal wound, a similar wrap, utilizing the same basic design with appropriate dimensional modifications, could be constructed quite easily for use with another anatomical part.

Because of its unique design and construction, the wrap of the present invention is exceptionally comfortable and may be worn continuously throughout the recovery process, even if lengthy. The completely adjustable upper and lower edges of the wrap may each be independently tightened or loosened as desired for comfort, as well as for secure retention of the primary dressing materials in place over the wound. In addition, use of this invention enhances patient compliance and involvement in their own treatment and personal care. As their recovery progresses, patients report that the present wrap continues to be quickly and easily adjustable to accommodate the changes that occur, such as the reduction in the overall bulk of bandaging as the size of the wound decreases with healing. Also, as presently embodied, the wrap may be laundered and disinfected by hand or machine for quick and economical re-use by the same patient.

DESCRIPTION OF THE PREFERRED EMBODIMENT

Figure 1:
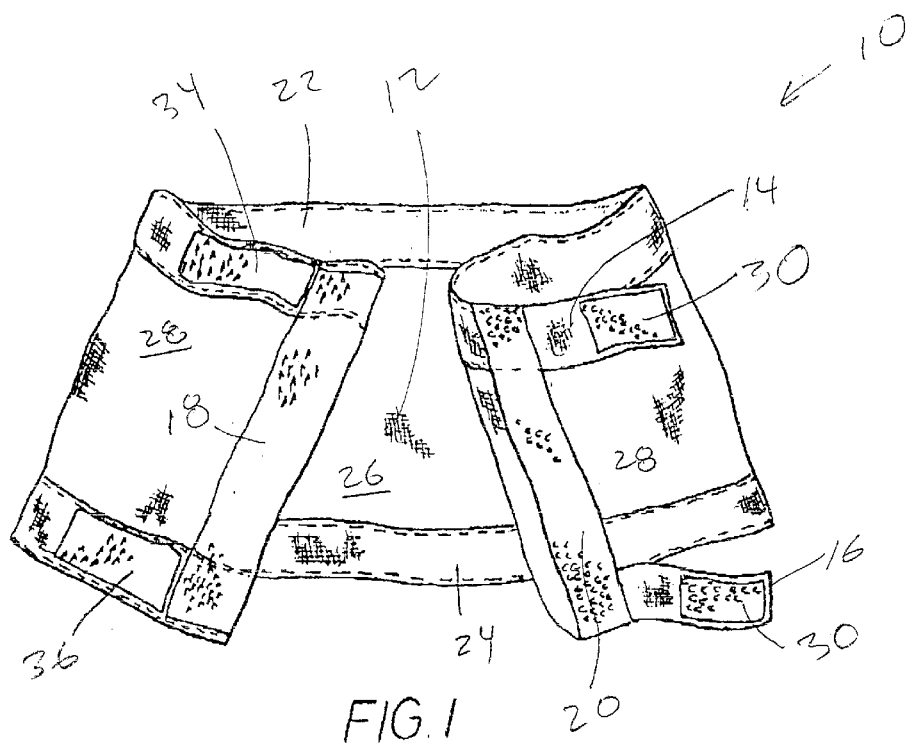
FIG. 1 is a perspective view of an adjustable dressing wrap made in accordance with the present invention.

As shown in FIGS. 1 through 4, the adjustable dressing wrap 10 has a generally rectangular shape and is made primarily of a four-way elastic, porous, micromesh material 12. In this preferred embodiment, the micromesh material 12 is a blend of improved nylon (Antron®) and spandex (Lycra®) fibers, has an exceptionally lightweight and stretchable hand, yet it is strong and durable.

The micromesh material 12 used in the embodiment of the adjustable dressing wrap 10 is also highly porous, thereby permitting the virtually unimpeded circulation of air to the underlying wound and primary dressing materials, and the substantial elasticity of the micromesh material 12 enables it to conform comfortably over the affected body part and dressings. This elasticity also enables the adjustable dressing wrap 10 to accommodate with ease the fluctuations in size of the wound and surrounding tissues occurring with treatment of the wound, as well as the adjustments in the amount and type of dressings used as healing progresses.

The body of the adjustable dressing wrap 10, constructed of micromesh material 12, is supported on a framework including upper and lower, horizontally-extending elastic members 14, 16, and left and right, vertically-extending hook-and-loop fastener, or Velcro®, members 18, 20. The micromesh material 12 defines upper and lower casings 22, 24, adjacent the top and bottom edges of the mesh material. In this embodiment, the casings 22, 24 are self-casings, which are formed by folding the micromesh material 12 onto itself and stitching it from left to right. These upper and lower self-casings 22, 24 receive the upper and lower, horizontally-extending elastic members 14, 16, respectively. The self-casings permit only the micromesh material 12 to come into contact with the patient's skin, thus minimizing the potential for skin irritation and abrasion.

The upper and lower elastic members 14, 16 are extended within their respective casings 22, 24. Each of the elastic members 14 and 16 has two ends. The first end of each elastic member is stitched to one end of the micromesh material 12, with the other end projecting from its respective casing 22, 24. Except at the end that is stitched to the wrap, the elastic members 14, 16 are freely movable relative to their respective casings 22, 24 and thus are capable of substantial tightening or loosening, as desired, relative to the body portion of the adjustable dressing wrap 10.

Figure 2:
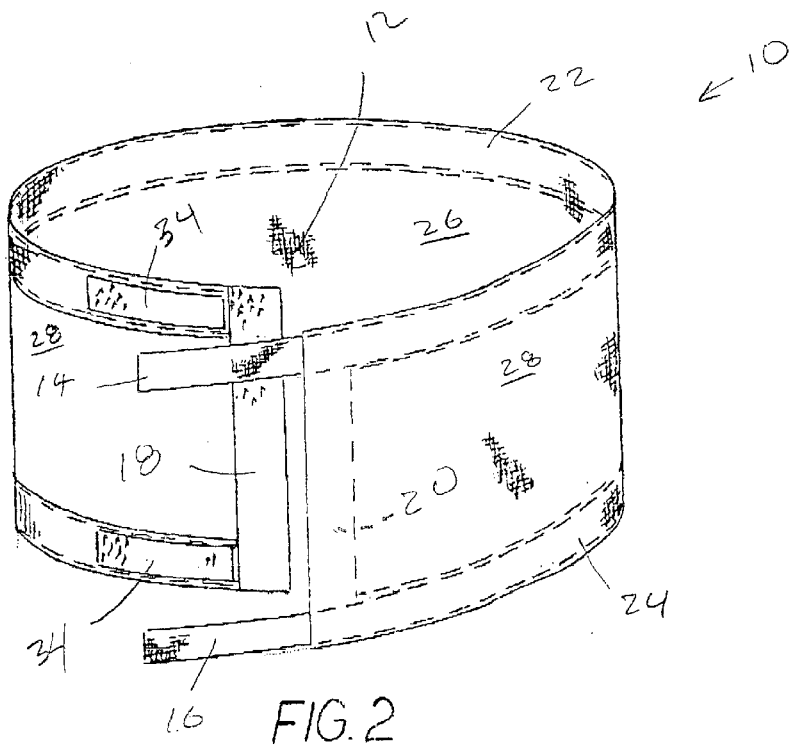
FIG. 2 is a perspective view of the wrap of FIG. 1.
Figure 3:
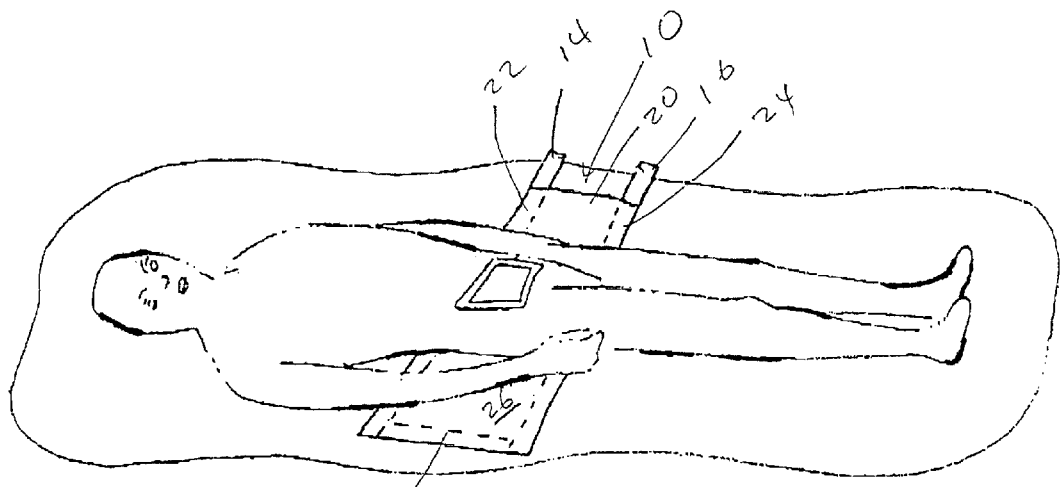
FIG. 3 is a perspective schematic of a patient with a dressing on his abdomen and the wrap as it is first being placed onto the patient; and, FIG. 4 is the same view as in FIG. 3 but with the wrap in place on the patient.
Figure 4:
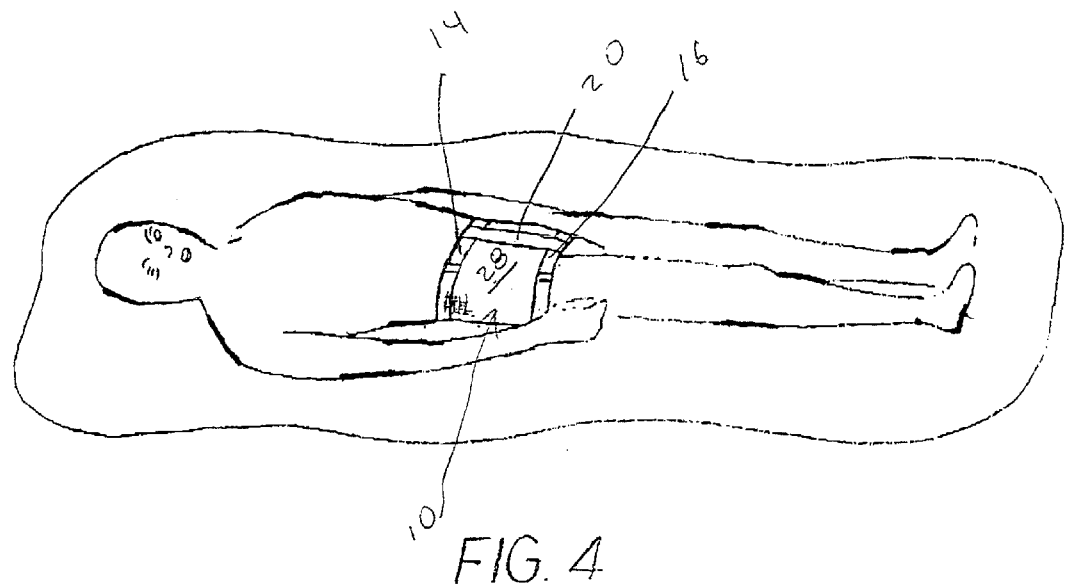

The micromesh material 12 body of the dressing wrap 10 has inner and outer surfaces 26, 28, respectively. In this embodiment, the hook portion of the hook-and-loop fastener (Velcro®) 20 is stitched onto the inner surface 26 at the right end of the micromesh material 12, while the loop portion of the fastener (Velcro®) 18 is stitched onto the outer surface 28 at the left end of the micromesh material 12. Thus, when the dressing wrap 10 is positioned around an anatomical part, as shown in FIG. 4, with the left and right vertically-extending hook-and-loop fastener members 18 and 20 overlapping, the fastener members 18 and 20 mate, securing the open vertical ends of the dressing wrap 10 together to form a longitudinal portion of the framework, extending from the upper edge to the lower edge of the dressing wrap 10, as depicted in FIG. 2.

The free end of each of the elastic members 14 and 16 has a hook portion 30 of a hook-and-loop fastener mounted on its inner surface. Corresponding loop portions 34 are mounted on the outer surface of the adjustable dressing wrap 10 at the left ends of the upper and lower casings 22 and 24. These loop portions 34 are elongated, preferably being longer than the corresponding hook portions 30. The hook portions 30 mate with their corresponding loop portions 34 of the hook-and-loop fasteners, and their relative positions may be adjusted to provide the desired amount of tension needed to fit snugly but comfortably over the primary wound dressing.

To use the adjustable dressing wrap 10, it is placed around the affected body part (in this embodiment, the torso) by a caregiver or the patient himself, if he is able, positioning the wrap 10 to encompass the primary wound dressing. The left and right vertical edges 18, 20 of the wrap 10 are brought into contact with each other, such that the hook-and-loop fasteners 18, 20 engage, forming a vertical portion of the framework of the adjustable dressing wrap 10. This vertical closing of the wrap 10 may be positioned wherever the patient finds it to be the most comfortable and convenient, e.g., directly over the primary wound dressing or, if that placement causes discomfort, to one side of the wound site.

Once the left and right edges 18, 20 are securely joined, then the upper and lower elastic members 14, 16 are adjusted and tightened around the affected body part to achieve the desired fit. They are then secured onto their respective hook-and-loop fastener patches 34, 36. In this manner, the encased circular elastic bands form firm upper and lower edges to the body of the wrap 10 and function, along with the vertical closing, to enable the wrap 10 to securely retain the primary dressing comfortably in position over the wound regardless of the physical activity level of the patient. The completely assembled wrap is shown in FIG. 4.

In this preferred embodiment of the wrap 10, the micromesh material 12 is thus seen to be supported on a framework that includes two substantially vertically-oriented fasteners 18, 20 along its left and right ends, and two substantially horizontally-extending elastic members 14, 16 in self-casings 22, 24 formed by hemming the edges of the micromesh material 12. Once assembled, this framework is substantially more rigid than the lightweight micromesh material 12.

The foregoing preferred embodiment has been set out in complete detail, but it will be understood that this is just one example of an adjustable dressing wrap made in accordance with the present invention. It will be obvious to those skilled in the art that numerous modifications and changes may be made to the embodiment described above without departing from the spirit and scope of the present invention as defined in the following claims.

What is claimed is:

1. A wrap for covering a wound dressing, comprising:
   a substantially rectangular member made of elastic, porous material defining top, bottom, left, and right edges and inner and outer surfaces;
   upper and lower casings formed adjacent to said top and bottom edges;
   upper and lower elastics extending within said upper and lower casings and freely movable relative to said casings, each of said elastics having at least a first free end projecting out from its respective casing beyond a first of said left and right edges of said rectangular member;
   a fastener mounted on the free end of each of said elastics;
   a hook portion of a hook-and-loop fastener mounted on and extending along one of said left and right edges; and
   a corresponding loop portion of a hook-and-loop fastener mounted on and extending along the other of said left and right edges, so that, when said left and right edges are overlapped, said hook portion and said loop portion mate to fasten said left and right edges together.

2. A wrap as recited in claim 1, wherein said substantially rectangular member is made of a material that is substantially more elastic than said hook-and-loop fastener portions.

3. A wrap as recited in claim 1, wherein said upper and lower casings are self-casings, formed by hemming the upper and lower edges of the rectangular member.

4. A wrap as recited in claim 1, wherein each of said elastics includes a second end secured to said substantially rectangular member adjacent to another of said left and right edges.

5. A wrap as recited in claim 4, wherein said hook-and-loop fastener portions extend substantially continuously along their respective left and right edges from the top edge of the member to the bottom edge of the member.

6. A wrap as recited in claim 5, wherein said substantially rectangular member is made of a micromesh elastic fabric including nylon and spandex fibers.

7. A wrap for covering a wound dressing, comprising:

a framework, including upper and lower, horizontally-extending elastic members, and left and right, vertically-extending hook-and-loop fastener members; and an elastic mesh material supported on said framework, wherein said mesh material defines upper and lower casings which receive said upper and lower, horizontally-extending elastic members, respectively, with at least a first free end of each of said elastic members projecting out of its respective casing beyond a first edge of said elastic mesh material and including one portion of a hook-and-loop fastener on said first free end, and said elastic mesh material defines left and right edges, with said vertically-extending hook-and-loop fastener members mounted on said left and right edges of said elastic mesh material, wherein said vertically-extending hook-and-loop fasteners are substantially more rigid than said elastic mesh material.

8. A wrap as recited in claim 7, wherein said elastic mesh material defines an outer surface and an inner surface; one of said vertically-extending hook-and-loop fastener members is mounted on the inner surface of its respective edge, extending substantially from the top edge to the bottom edge, and the other of said vertically-extending hook-and-loop fastener members is mounted on the outer surface of its respective edge, extending substantially from the top edge to the bottom edge, so that, when the left and right edges overlap, said vertically-extending hook-and-loop fastener members mate with each other to form a vertical closure extending substantially from the top edge to the bottom edge of said wrap.

9. A wrap as recited in claim 8, wherein each of said horizontally extending elastic members has a second end secured to said elastic mesh material adjacent to a second edge of said elastic mesh material.

\* \* \* \* \*